(12) United States Patent
Beck et al.

(10) Patent No.: US 9,109,391 B2
(45) Date of Patent: Aug. 18, 2015

(54) METHOD AND BRANCHING DETERMINATION DEVICE FOR DETERMINING A BRANCHING POINT WITHIN A HOLLOW ORGAN

(75) Inventors: Thomas Beck, Forchheim (DE); Christina Biermann, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 1030 days.

(21) Appl. No.: 12/693,556

(22) Filed: Jan. 26, 2010

(65) Prior Publication Data
US 2010/0189333 A1 Jul. 29, 2010

(30) Foreign Application Priority Data
Jan. 28, 2009 (DE) .......................... 10 2009 006 416

(51) Int. Cl.
| | | |
|---|---|---|
| *G06K 9/00* | (2006.01) | |
| *E06B 5/16* | (2006.01) | |
| *E06B 3/56* | (2006.01) | |
| *E06B 3/263* | (2006.01) | |
| *E06B 3/70* | (2006.01) | |

(52) U.S. Cl.
CPC . *E06B 5/161* (2013.01); *E06B 3/56* (2013.01); *E06B 2003/2631* (2013.01); *E06B 2003/7078* (2013.01)

(58) Field of Classification Search
CPC ................................. E06B 5/161; G06K 9/00
USPC ......................................................... 382/128
See application file for complete search history.

(56) References Cited

U.S. PATENT DOCUMENTS

| | | | |
|---|---|---|---|
| 4,656,665 A * | 4/1987 | Pennebaker .................. 382/172 |
| 2001/0031920 A1* | 10/2001 | Kaufman et al. ............. 600/431 |
| 2004/0252870 A1* | 12/2004 | Reeves et al. ................ 382/128 |
| 2006/0088198 A1* | 4/2006 | Arnold ......................... 382/131 |
| 2008/0187199 A1 | 8/2008 | Gulsun |
| 2009/0306644 A1* | 12/2009 | Mayse et al. .................... 606/33 |
| 2010/0159497 A1* | 6/2010 | Kimia et al. ................... 435/29 |

OTHER PUBLICATIONS

Haris, K et al., "Model-based Morphological Segmentation and Labeling of Coronary Angiograms", IEEE Trans. on Medical Imaging, vol. 18, Nr. 10, Oct. 1999, S. 1003-1015; Others; 1999.

(Continued)

*Primary Examiner* — Hiep V Nguyen
*Assistant Examiner* — Trang Nguyen
(74) *Attorney, Agent, or Firm* — Harness, Dickey & Pierce, P.L.C.

(57) ABSTRACT

A method is disclosed for determining a branching point within a hollow organ in image data representing the spatial structure thereof. In at least one embodiment, the method includes setting a start point within the hollow organ; determining at least one local threshold which corresponds to the presence of a wall of the hollow organ; carrying out a region growing method using the threshold; analyzing the connectivity of a number of outer growth layers; and localizing a branching on the basis of the connectivity analysis. Moreover, at least one embodiment of the invention relates to a correspondingly designed branching determination unit.

21 Claims, 10 Drawing Sheets

(56) References Cited

OTHER PUBLICATIONS

Pisupati, C., et al., "A Central Axis Algorithm for 3D Bronchial ZTree Structures", Symp. on Computer Vision, Proceedings, Nov. 21-23, 1995, S. 259-264; Others; 1995.

Yim, P.J., et al., "Gray-Scale Skeletonization of Small Vessels in Magnetic Resonance Angiography", IEEE Trans. on Medical Imaging, vol. 19, Iss. 6, 2000, S. 568-576; Others; 2000.

* cited by examiner

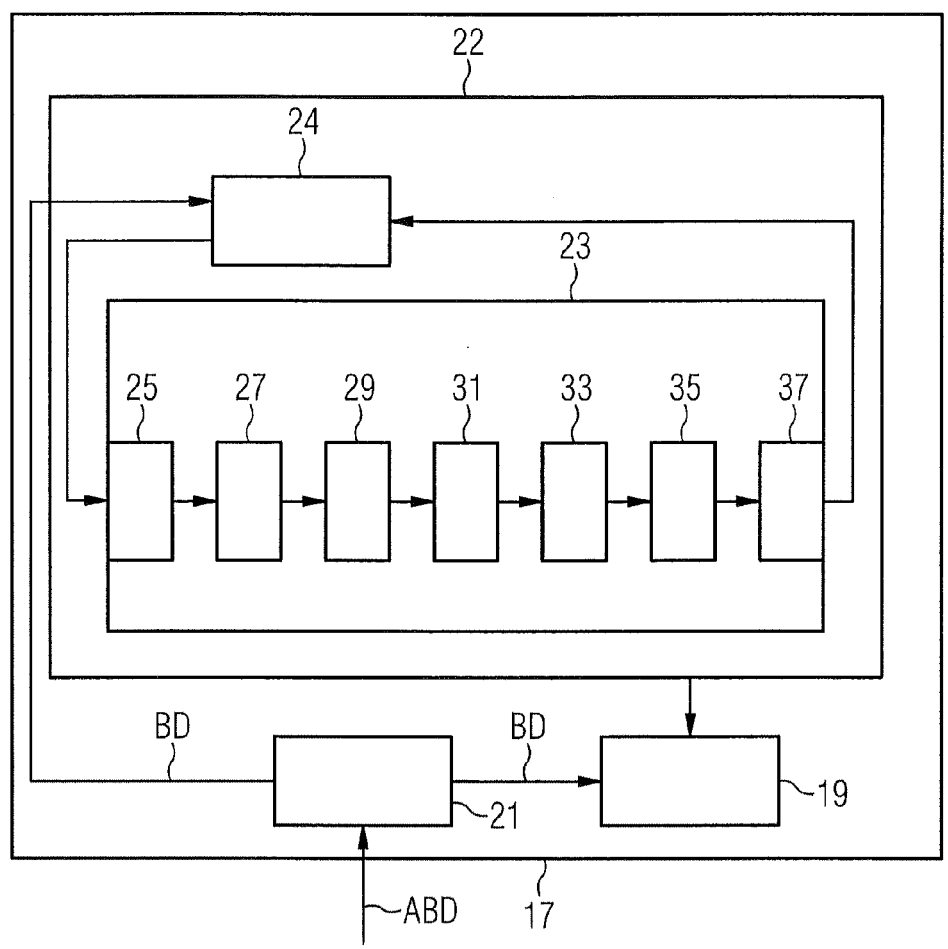

METHOD AND BRANCHING DETERMINATION DEVICE FOR DETERMINING A BRANCHING POINT WITHIN A HOLLOW ORGAN

PRIORITY STATEMENT

The present application hereby claims priority under 35 U.S.C. §119 on German patent application number DE 10 2009 006 416.8 filed Jan. 28, 2009, the entire contents of which are hereby incorporated herein by reference.

FIELD

At least one embodiment of the present invention generally relates to a method for determining a branching point within a hollow organ in image data representing the spatial structure thereof. Moreover, it relates to a corresponding branching determination device.

BACKGROUND

Determining branching points of hollow organs plays an important role in determining a center line through the hollow organ, which line in turn constitutes a central component in the analysis of the hollow organs. Thus, these days, the interior of hollow organs, for example intestines or blood vessels, are visualized using the so-called virtual flight. In the process, a particular challenge is to set the center line precisely in the center within the lumen of the hollow organ.

This is particularly important in angiography, for example in computed tomography angiography (CTA), which enables the detection of deformations of vessels, e.g. stenoses or aneurysms. This is because in this case it is necessary for the dimensions of the lumen, that is say in particular the cross sections or radii of the vessels, to be precisely measured as precisely as possible such that a user can draw conclusions in respect of the type and degree of the deformation from these specifications. The precise measurement in turn requires the extent of the lumen to be measured perpendicularly with respect to the vessel profile because otherwise there could be erroneous interpretations with grave consequences. The vessel profile is in turn represented by the center line of the hollow organ and so the latter must be determined as precisely as possible.

The center lines of hollow organs are currently determined using different, graph-based methods. They are usually based on the A* algorithm or Dijkstra's algorithm, wherein the image data of the hollow organ is interpreted as a graph and, in the process, voxels are considered to be nodes with six further voxels being in the direct three-dimensional neighborhood thereof. These are inserted into the graph by being connected by edges. Using a cost function based on local grayscale values of CT image data, the weighting of the individual edges is identified and the costs for reaching a target point are determined on the basis of an underlying heuristic.

This method does not consider any knowledge relating to the geometry of the hollow organ. As a result of this, erroneous segmentations can occur within the scope of the method, particularly if the hollow organ is observed in a region in which other hollow organs or bone structures are situated in the vicinity. However, in particular, it is not possible for a distinction to be made between unbranched and branching regions of the hollow organ.

SUMMARY

At least one embodiment of the invention provides a method which is as efficient and precise as possible and a branching determination device for determining a branching point in a hollow organ which, in particular, is very precise and as little error prone as possible.

A method of at least one embodiment includes:

a) Setting a start point within the preferably tubular hollow organ. By way of example, a point entered by a user via an input interface—e.g. a seed point, a line or a plane—can in this case be used as a start point. This start point can preferably be checked—possibly automatically—with respect to the suitability thereof as a start point for the method and, if need be, be suitably adapted before carrying out the further steps, for example if a seed point was inadvertently placed outside of the hollow organ. Alternatively, a logic unit can also automatically set the start point in an independent fashion on the basis of detection algorithms.

b) Determining at least one local threshold in the region around the start point, which threshold corresponds to the presence of a wall of the hollow organ. For this, pixels and/or voxels in a region around the start point are preferably analyzed. This analysis is used to differentiate the image data and distinguish between pixels or voxels which represent regions within the hollow organ and those which are situated outside of the organ (in doing so—as is also the case in the following text—pixels in a two-dimensional illustration can represent voxels). In the process, the threshold preferably relates to the intensity values of the pixels or voxels, i.e. at least one threshold is sought after, by means of which a decision can be made as to whether said pixel or voxel is part of the interior of the hollow organ or part of the wall or a region external thereto on the basis of the present intensity value of a pixel or voxel. Determining the threshold can comprise the derivation thereof from the circumstances around the start point, for example with the aid of the just-described pixel or voxel analysis. However, it can also comprise obtaining a threshold which has a high probability of also being valid in the region around the start point, for example from a database or from analyzing a region around a different examination point in the vicinity of the start point. By way of example, if the method according to the invention is carried out a number of times, a representative threshold determined previously for a different start point can be utilized again.

c) Carrying out a region growing method using the threshold. In the region growing method, the directly adjacent pixels or voxels are examined, starting from the start point. If the intensity values of said pixels or voxels are within the region defined by the threshold, they are connected to the start point to form a region. The method is then continued outwardly, layer-by-layer, up to a certain, preferably predefined, number of layers. That is to say the region growing method combines all pixels or voxels which are to be associated with the interior of the hollow organ into a region.

d) Analyzing the connectivity of a number of outer growth layers. In the process, one or more outer pixel or voxel layers are examined to that effect of whether all pixels or voxels are connected. In other words, an examination is carried out as to whether each pixel or voxel to be associated with a growth layer or a number of growth layers has an adjacent pixel/voxel which is a member of the same (number of) growth layer(s).

e) Localizing a branching on the basis of the connectivity analysis. A branching is preferably localized if a predetermined number of outer growth layers are no longer completely connected because what emerges from this recognition is that a wall is situated between two connected clusters of the (number of) growth layer(s) and this indicates that the hollow organ branches at said locations.

As a result of using thresholds, the method can be carried out very effectively and accurately. Combined with the region growing method and the connectivity analysis, this results in a very reliable detection of branchings.

A branching determination device according to at least one embodiment of the invention for determining a branching point within a hollow organ at least comprises:

an input interface for image data representing a spatial structure of the hollow organ, a start point setting unit for setting a start point within the hollow organ, a threshold determination unit for determining local thresholds in the region around the start point, a region growing unit for carrying out a region growing method, a connectivity analysis unit for analyzing the connectivity of a number of outer growth layers, a localization unit for localizing a branching as a function of the connectivity analysis, and preferably also an output interface for transmitting localization data from the localization.

The mentioned interfaces do not necessarily have to be designed as hardware components but can also be implemented as software modules, for example if the image data can be taken from another component already implemented on the same equipment, e.g. from an image reconstruction apparatus of another image processing unit or the like, or if the localization data only has to be transmitted in software terms to another component. Likewise, the interfaces can comprise hardware and software components, for example a standard hardware interface which has been configured specifically by software for this particular use. Moreover, they can also be combined together with other interfaces in a combined interface, for example an input-output interface.

Overall, a majority of the components for implementing the branching determination device according to at least one embodiment of the invention can wholly or partly be implemented in the form of software modules on a processor, in particular the setting unit, the threshold determination unit, the region growing unit, the connectivity analysis unit, and the localization unit.

The branching determination device is preferably designed such that it can independently carry out a method according to at least one embodiment of the invention in a fully-automated fashion. However, it can also operate in a semi-automatic fashion, i.e. it is supplied with necessary additional information by an additional input from the outside, for example from further logic units possibly connected to databases or from manual inputs by an operator. This input can for example relate to the localization of a start point for the region growing method. In this case, the setting unit in particular can comprise an input interface for external input, by means of which information in respect of the start point can be obtained.

At least one embodiment of the invention also comprises a computer program product which can be loaded directly into a processor of a programmable image processing device, with program code means for executing all steps of a method according to at least one embodiment of the invention when the program product is executed on the image processing device.

Further particularly advantageous refinements and developments of the invention emerge from the dependent claims and the following description. In the process, the branching determination device can also be developed in a corresponding fashion to the dependent claims in respect of the method.

A plurality of radial search beams are preferably defined from the start point for determining a local threshold and the intensity values of the pixels and/or voxels are determined along these search beams. In the process, a plurality of search beams are "emitted" in a virtual fashion from the initial position, the directions of said beams preferably affording the possibility of covering space in three dimensions and the lengths of which beams being particularly preferably selected such that at least the majority of said beams pass through the wall of the hollow organ. Therefore, the definition of these search beams is also referred to as "emission" in the following text. The search beams which do not penetrate the wall of the hollow organ over their entire length—for example because they are basically situated parallel to the profile of the hollow organ—are preferably ignored from here on in. Instead of having to examine all voxels or pixels of an image data record or in a defined, sufficiently large neighborhood of the start point, the wall dimensions of the hollow organ are determined by selection analysis of the voxels or pixels along the (selected) search beams in a representative fashion. If these search beams have a defined length, the number of pixels or voxels to be examined is limited precisely as a result of the number of search beams and their fixed lengths, and, advantageously, it is significantly smaller than in the case of examining all pixels in a neighborhood region of the same extent.

At least 72 radial search beams are preferably emitted from the start point. Empirical investigations by the inventors have shown that a sufficiently representative spatial cover of hollow organs can be obtained by using this number of search beams. In the process, the search beams should preferably be emitted such that they are evenly distributed in space. That is to say there is the same solid angle between them in space in each case so that an even cover can be obtained in all dimensions and directions.

A histogram, e.g. of pixel or voxel intensity values along search beams derived from a common initial position, is preferably analyzed for determining a local threshold. The histogram analysis advantageously comprises estimating the local threshold using a maximum likelihood method. Using this procedure, the image data can easily be analyzed along search beams and the wall of the hollow organ can be fixed on the basis of established estimation methods where the local thresholds are respectively attained using the grayscale value profile along such search beams.

In addition to determining the threshold, at least one embodiment of the invention uses the method steps of the region growing method and the connectivity analysis. In principle, this analysis can in this case respectively only analyze the connectivity of an individual, to be precise the outermost, growth layer from the region growing method. However, a plurality of individual outer growth layers, for example the last two or three, are preferably analyzed together in respect of connectivity. This can at least significantly reduce the number of false-positive detections of branchings. By way of example, stenoses or aneurysms can lead to the surface of a hollow organ being so uneven that the outermost growth layer—or even a plurality of layers—is no longer connected. Only when analyzing the connectivity of a plurality of outer growth layers, at least three growth layers are particularly preferred, it can be seen that it is not a branching but only unevenness, e.g. a thickening or a recess, that is present.

Furthermore, it is preferable for the connectivity to be analyzed beyond a defined pixel and/or voxel spacing between the outermost growth layer and the start point. This procedure saves computational capacities and is advantageous, particularly if the determination method according to at least one embodiment of the invention is repeatedly carried out from different start points. It can then be assumed that the first growth layers were already analyzed in respect of their connectivity at an earlier time in conjunction with a preceding start point.

The connectivity analysis preferably comprises cluster analysis with a distance function. This is particularly preferably analysis of the minimum distance between two elements from different clusters, that is to say the so-called "single linkage clustering". The cluster analysis and, in particular, the "single linkage clustering" constitute simple and reliable methods (because they are established and tested methods) of analyzing connectivity which can be applied without problems in the application in the method according to at least one embodiment of the invention.

Particularly advantageous effects emerge from within the scope of the method according to at least one embodiment of the invention if additional information is derived from the spatial information relating to the localized branching and generated by the method. Firstly, a branching center point can be determined from spatial information in respect of the localized branching. The branching center point is preferably defined by the centroid of all pixels or voxels of all growth layers constructed up to the detection of the branching. When forming the centroid, every pixel or voxel is preferably included with the same weighting and with its positional data. Secondly, the branching center point can be derived automatically or semi-automatically from the information already present, namely in respect of the position of the growth layers. The branching center point is particularly preferably defined as the centroid of all growth layers constructed up to the detection of the branching.

Analogously, an initial center point of a hollow organ strand after the branching can advantageously also be determined from spatial information in respect of the localized branching. By way of example, this is effected by the initial center point of the hollow organ strand being formed as a function of the centroid of a cluster of a number of outer growth layers identified in the above-described method. The cluster is formed by local parts of growth layers, preferably by the entirety thereof, which are situated in the region of an individual hollow organ strand and no longer form a connected growth layer within the scope of the region growing method. In other words, the centroid, which is particularly preferably considered to be the initial center point of the hollow organ strand, is formed by those parts of the growth layers which are already situated in the branched hollow organ strand.

Using the center point specifications in respect of the branching center point or the initial center points determined in this fashion, a center line of the hollow organ can also be led through a branching region of a hollow organ. The invention therefore also comprises a method for determining a center line of a section of a hollow organ in image data in the region of a branching point of the hollow organ, wherein the center line is led through a branching center point determined in a method according to the invention and/or through an initial center point determined in a method according to at least one embodiment of the invention. Accordingly, at least one embodiment of the invention also comprises a computer program product which can be loaded directly into a processor of a programmable image processing system, with program code segments/modules for executing all steps of a method according to at least one embodiment of the invention for determining a center line when the program product is executed on the image processing system.

BRIEF DESCRIPTION OF THE DRAWINGS

In the following text, the invention will once again be explained in more detail on the basis of example embodiments, with reference to the attached figures. In the process, the same components have been provided with identical reference signs in the various figures. Herein:

FIG. 14 shows a schematic block diagram of an example embodiment of an image processing device with a branching determination device according to the invention.

DETAILED DESCRIPTION OF THE EXAMPLE EMBODIMENTS

Figure 1:
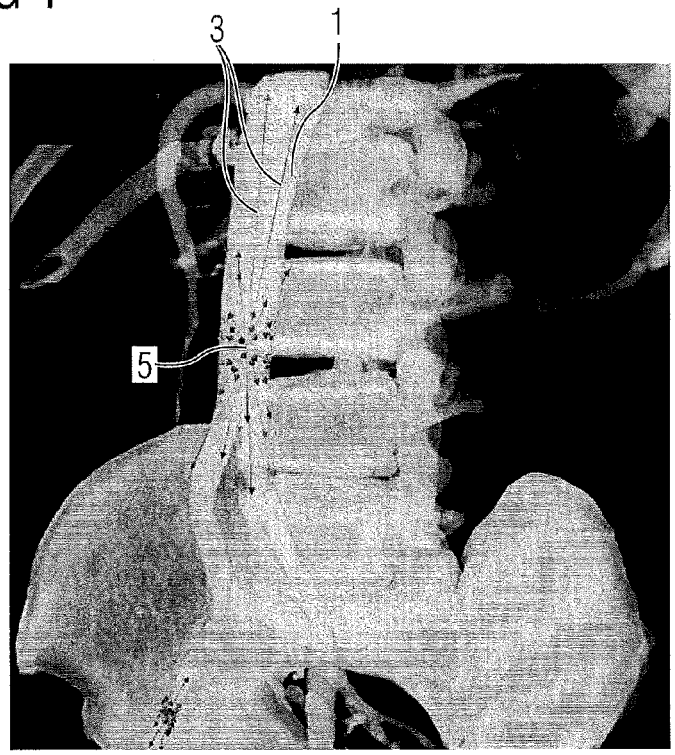
FIG. 1 shows an illustration of image data, obtained using a computed tomography method, showing a pelvic region with the bony structures of a pelvis and part of a spine, together with a section of a hollow organ.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Without loss of generality the following text illustrates an example embodiment of a method for determining a center line of a hollow organ combined with the method according to the invention for detecting the branching of the hollow organ.

FIG. 1 shows a display of a recording of a human pelvic region on the monitor of a diagnostic station. In addition to the bone structures of the pelvis and part of the spine, it shows a section of a hollow organ 1, in this case a blood vessel, with the center line thereof intended to be determined. It has relatively long unbranched regions and a number of branchings, for example in the center of the image and in the lower image region.

In an advantageous center line determination method, a start point 5, in this case an individual seed point, is set within the hollow organ, for example by user input via a user interface of the diagnostic station on the basis of image data of the blood vessel 1, which image data is preferably available as volume image data. Search beams 3 are emitted with an even spatial distribution from this seed point 5.

Figure 2:
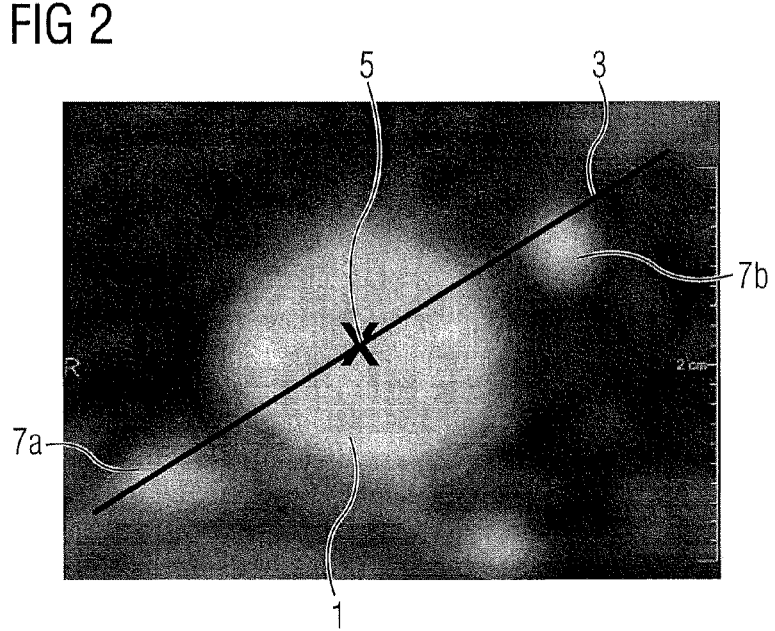
FIG. 2 shows a slice image through a hollow organ with an individual search beam.
Figure 3:
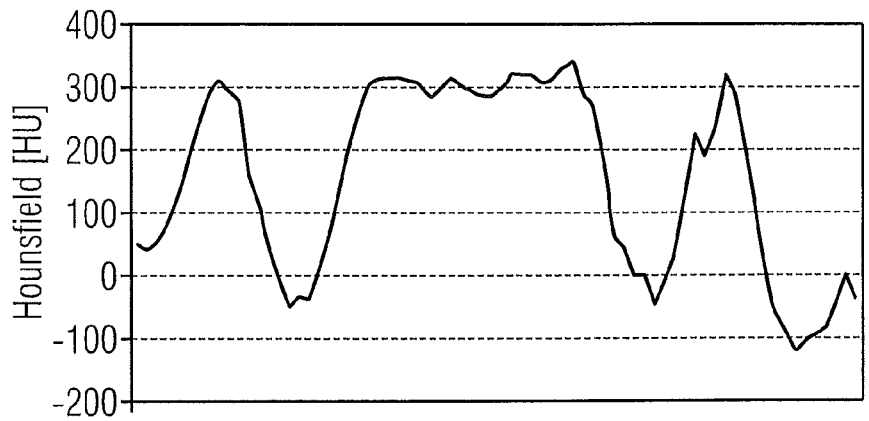
FIG. 3 shows the attenuation profile of the hollow organ in FIG. 2 along the search beam.

Within a cross section of a hollow organ 1, an individual such search beam 3 is shown in FIG. 2. It traverses the hollow organ 1 and then passes through the surrounding tissue, with further cross sections of structures 7a, 7b running approximately parallel to the hollow organ 1 in this region being situated on both sides of the hollow organ 1 along the search beam, with the latter likewise penetrating said structures. As illustrated in FIG. 3, a Hounsfield profile is generated along the search beam 3. It can be seen that the Hounsfield values of the surrounding tissue are significantly lower than those of the hollow organ 1 and the structures 7a, 7b.

Figure 4:
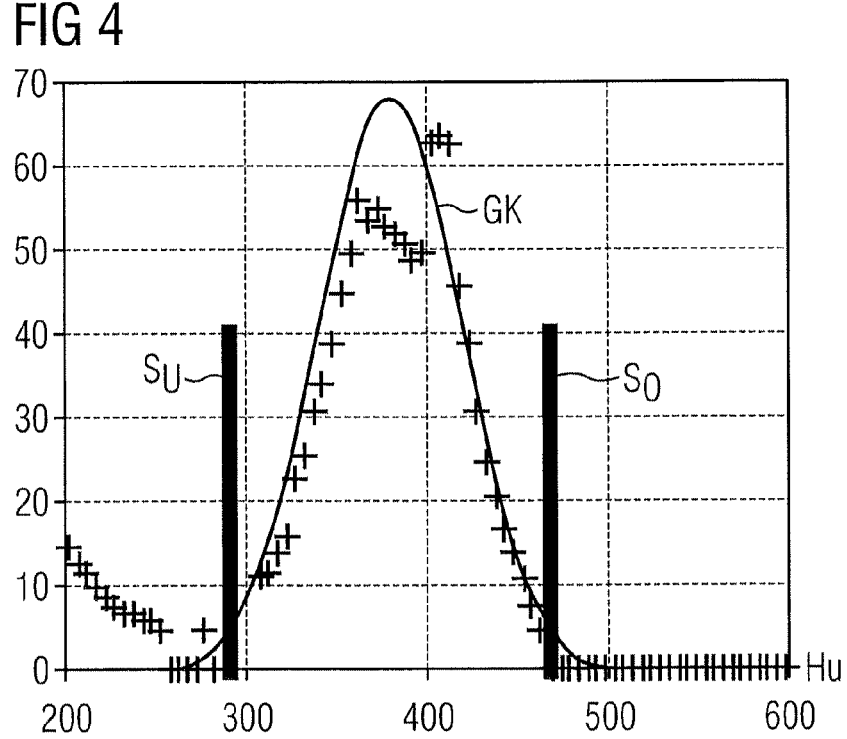
FIG. 4 shows a local histogram of a hollow organ region with a distribution curve for determining thresholds fitted thereto.

A local histogram can subsequently be generated for all pixels or voxels situated along all search beams; said histogram is illustrated in FIG. 4. Each cross respectively shows (plotted on the y-axis), in absolute numbers, the number of voxels of all search beams having a certain grayscale value intensity, the latter being plotted on the x-axis in Hounsfield units. A Gaussian curve GK, suitable in terms of its shape and representing the value distribution logic of the histogram, was fitted to the histogram using a maximum likelihood method. A lower and an upper threshold $S_u$ and $S_o$ were derived as a function of the shape of the Gaussian curve GK, that is to say of the standard deviation $\sigma$ and the mean value $\mu$ thereof. These thresholds $S_u$, $S_o$ are at $$S_u = \mu - 2*\sigma \text{ and } S_o = \mu + 2*\sigma.$$

The Hounsfield range between the thresholds $S_u$, $S_o$ defines the interval (cf. FIG. 3) in which Hounsfield values of the hollow organ to be examined typically lie.

Hounsfield values outside of this range are considered not to belong to the hollow organ.

Figure 5:
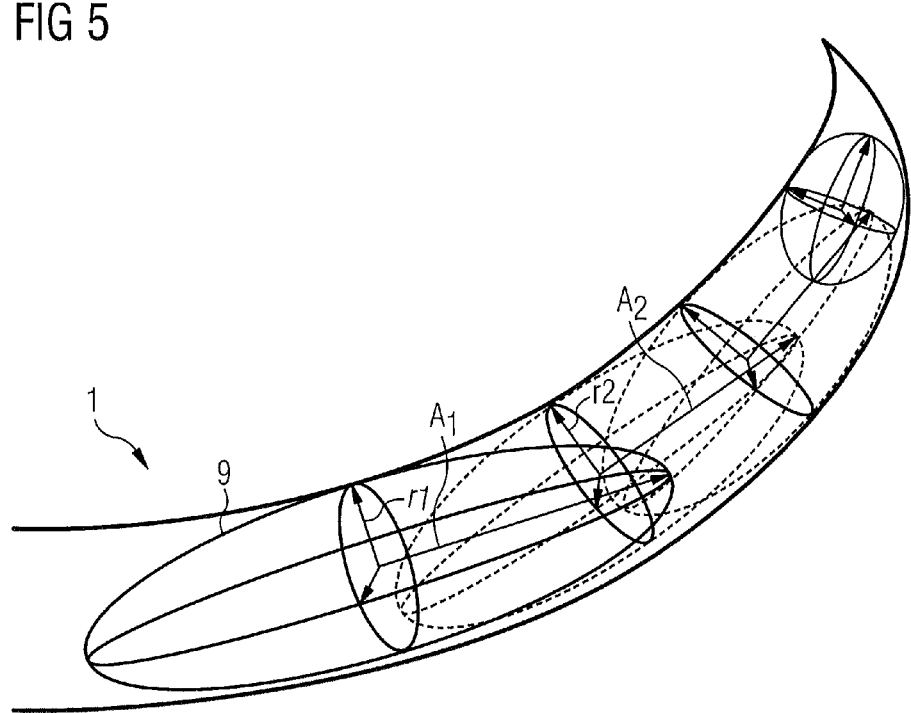
FIG. 5 shows a schematic illustration of a hollow organ section with geometric figures fitted therein.

FIG. 5 schematically shows a section of a hollow organ 1 into which mutually overlapping geometric figures, in this case ellipsoids 9, are fitted. The shape and size of the ellipsoids emerges from principle component analysis of a point cloud of penetration points through the wall of the hollow organ along the search beams (cf. FIG. 1). These penetration points were placed where the voxel values of the respective search beams leave the Hounsfield range between the thresholds $S_u$, $S_o$ (cf. FIG. 4) for the first time.

Each fitted ellipsoid can be characterized by a radius $r_1$, $r_2$, ..., $r_n$ and a principle axis $A_1, A_2, ..., A_n$. Within the scope of this example embodiment, the next start point in the form of a new seed point is also set along the respective principle axis $A_1, A_2, ..., A_n$, provided that the potential start point is not situated in a branching region. The new seed point is then situated on the respective principle axis $A_1, A_2, ..., A_n$, offset by half of the respective radius $r_1, r_2, ..., r_n$ in a progression direction in which a center line of the hollow organ section is intended to be determined. On the basis of the respective new start point, a row of ellipsoids is fitted into the hollow organ section by recursive repetition of the described method (from emitting the search beams to fitting a new ellipsoid and determining a new start point), the center points of which ellipsoids defining the center line of the hollow organ section. Thus, a curved curve which represents the center line can for example be placed passing through the center points.

Figure 6:
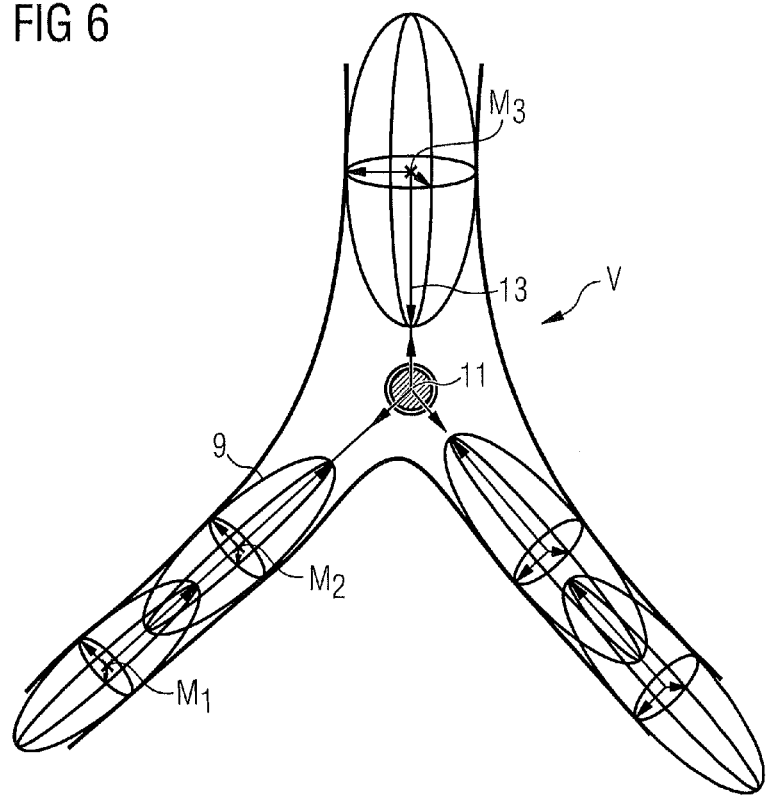
FIG. 6 shows a schematic illustration of a hollow organ section with geometric figures fitted therein in a branching region of the hollow organ section.

A peculiarity emerges in the determination of the center line when a branching region V as illustrated schematically in FIG. 6 is reached. In the process, it is first of all necessary to even recognize the branching region V because the reconstruction of a center line 13 according to the previously described method is predominantly suitable for unbranched hollow organ regions. Moreover, the branching center point 11 is required for the continuation of the center line 13. The method according to the invention, explained in more detail on the basis of FIGS. 7 to 9, is used for both recognizing the branching region V and for identifying the branching center point 11.

Figure 7:
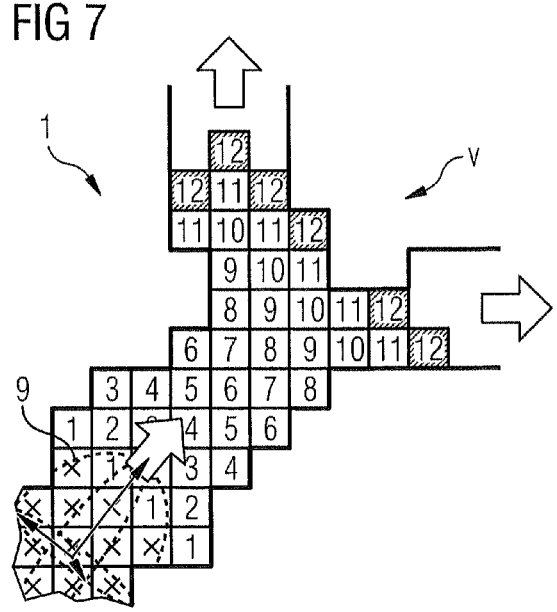
FIG. 7 shows a schematic illustration of a region growing method in the branching region whilst carrying out branching recognition according to a first embodiment.

FIG. 7 schematically illustrates a first embodiment of a method according to the invention for determining a branching point V. This method is preferably always carried out before the principle component analysis is carried out and has particularly preferably already been carried out before the search beams are defined from a new start point. If no branching point is recognized in the process, a new geometric figure is fitted into the hollow organ as described further above.

When a branching point is determined according to an embodiment of the invention, a region growing method is carried out starting from a start point identified as described above by the shape of the last ellipsoid 9. Growth layers of the first to the n-th order are constructed within the hollow organ on the basis of the previously identified local thresholds $S_u$, $S_o$ defining a Hounsfield range associated with the organ. In the process, connectivity is analyzed in the present embodiment in the n-th growth layer after carrying out the growing step. According to this analysis, a branching point V is present if the outermost growth layer—the twelfth growth layer in FIG. 7—is no longer completely connected. By contrast, there is no branching in the examination region if a number of outer growth layers are respectively connected; the number is determined as a function of the radius of the last-identified ellipsoid 9. Thus, the growth depth is preferably adjusted according to the radius of the preceding ellipsoid 9 or the analogously selected dimensional specifications of other geometric figures. Thus, the growth depth can be adjusted dynamically—for example as a function of the lumen of the hollow organ.

Figure 8:
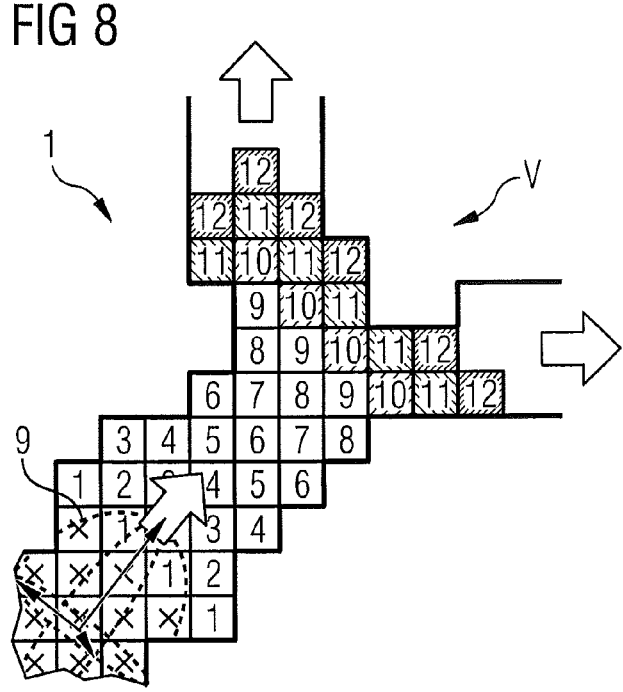
FIG. 8 shows a schematic illustration of a region growing method in the branching region whilst carrying out branching recognition according to a second embodiment.
Figure 9:
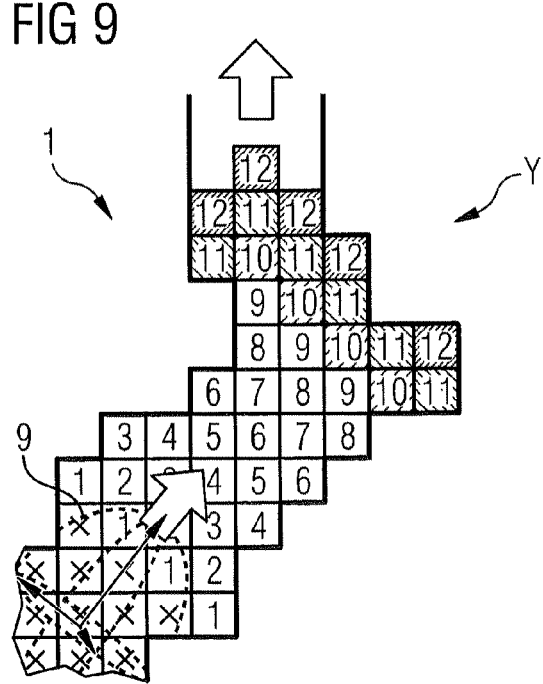
FIG. 9 shows a schematic illustration of a region growing method in an unbranched region with a bulge.

FIG. 8 illustrates a second embodiment of a method according to the invention for determining a branching point V; it has less sensitive recognition logic but as a result is also less error prone. Here, instead of the outermost growth layer being analyzed, a plurality of outer growth layers—two layers in the present case—are analyzed in respect of their connectivity. That is to say the signal that a branching point V is present is only generated once the two outer layers 11 and are no longer connected. As a result of this slightly rougher connectivity analysis logic, the generation of false positive signals can be avoided, for example if the hollow organ only has a recess or a bulge which could incorrectly be recognized as a branching point in the case of a very fine analysis.

Figure 10:
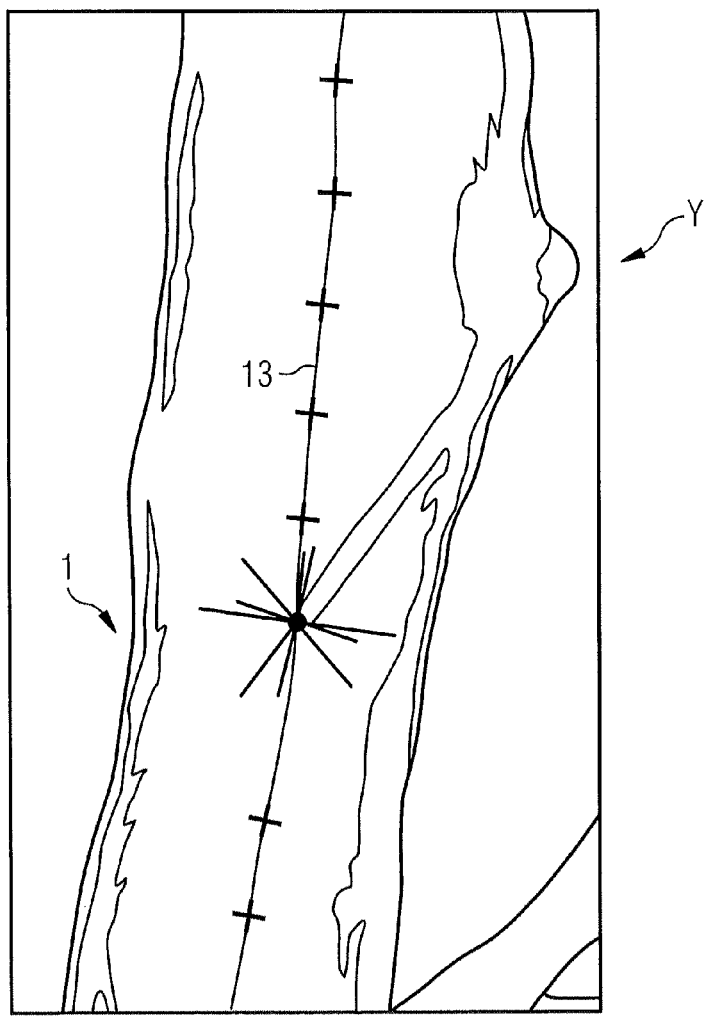
FIG. 10 shows an illustration of such an unbranched region with a bulge from image data obtained by way of a computed tomography method.

FIGS. 9 and 10 are used to illustrate the necessity of a differentiated recognition logic of branching regions. Thus, in an analogous fashion to FIG. 8, FIG. 9 shows a hollow organ 1 in which growth layers were constructed using the region growing method. However, instead of the branching region V, only a bulge Y of the hollow organ 1 is situated at approximately the same position. A connectivity analysis of only the outermost growth layer 12 would lead to the erroneous conclusion that a branching region was present for this bulge Y. By contrast, a combined analysis of the three outer growth layers 10-12 can avoid this false-positive conclusion.

An analog counterpart in the real image recorded by computed tomography is shown in FIG. 10; herein a hollow organ 1 in turn has a bulge Y in the upper right image region.

Figure 11:
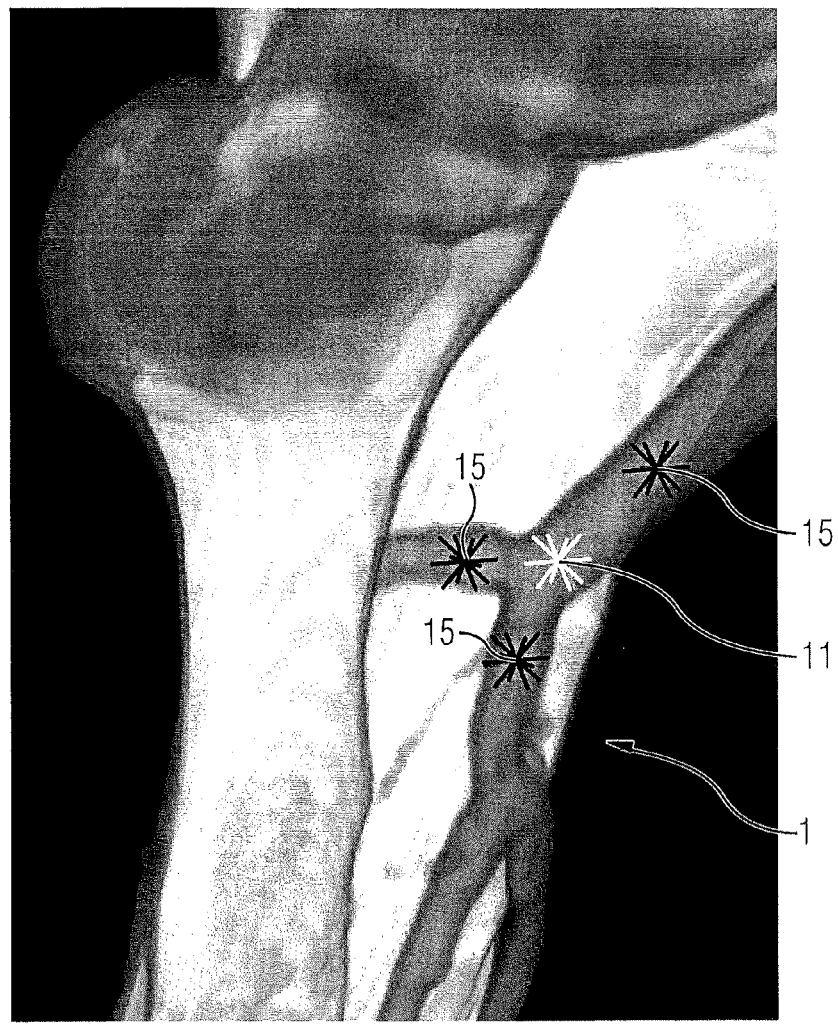
FIG. 11 shows an illustration with a hollow organ section from computed tomography image data with a branching center point and three initial center points of the three hollow organ strands being marked in the region of the branching.

Using the recognition logic for branching points V described on the basis of FIGS. 7 and 8, it is subsequently also possible for the branching center point 11 and initial center points 15 of hollow organ strands to be set downstream of the branching point V, as illustrated in FIG. 11. The centroid of all growth layers constructed up to the detection of the branching, i.e. the centroid of growth layers 1 to 12 in the examples of FIGS. 7 and 8, is preferably used as the branching center point 11. Since the start point of the region growing method cannot be placed at an arbitrary distance from a branching point V (because otherwise e.g. a further ellipsoid could be fitted into an unbranched region), the centroid can approximately represent the branching center point 11 of the branching point V.

A similar result holds true for the initial center points 15. They are formed by the centroid of a cluster of the number of outer growth layers, wherein the cluster is formed from such local parts of growth layers which are situated in the region of the individual hollow organ strand and which no longer form a connected growth layer within the scope of the region growing method. Staying with the image in FIGS. 7 and 8, the initial center point of the hollow organ strand leaving to the right would be formed in FIG. 7 by the centroid of the two voxels in layer 12 and in FIG. 8 by the centroid of the four voxels in layers 11 and 12 in this hollow organ strand. This can mean that precisely this centroid is used as an initial center point 15 of the hollow organ strand or that said centroid is used as the initial variable for the more precise identification of the exact initial center point which can then in turn be carried out within the scope of the above-described method for identifying the center line with the aid of the ellipsoids. In other words: an initial center point 15 of a hollow organ determined as described above can subsequently again serve as a start point for carrying out a method according to the invention for further determination of the center line 13.

Figure 12:
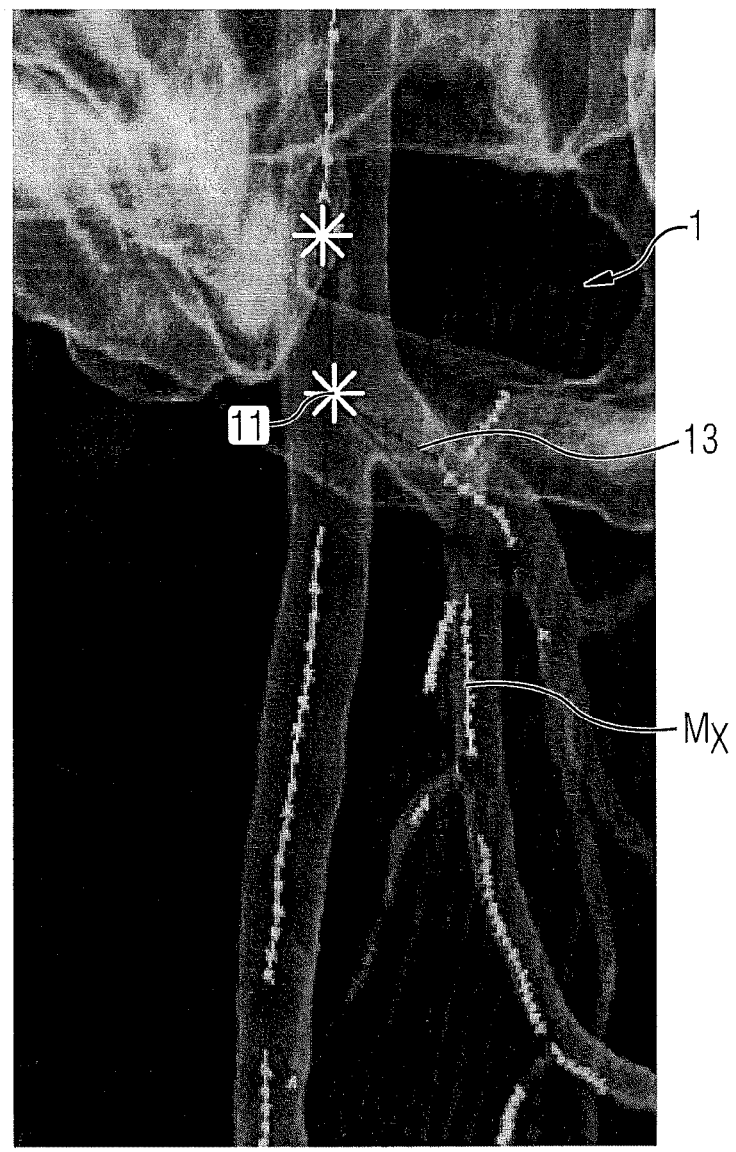
FIG. 12 shows an illustration of a hollow organ section from computed tomography image data with the center line thereof being marked.

In the end, this results in a center line 13 as illustrated in FIG. 12 at the end of the methods for identifying the center line or for determining branching points of a section of a hollow organ 1: said center line 13 is defined by branching center points 11 and by center points $M_x$ of the ellipsoids (not illustrated in this figure) to which it is oriented.

Figure 13:
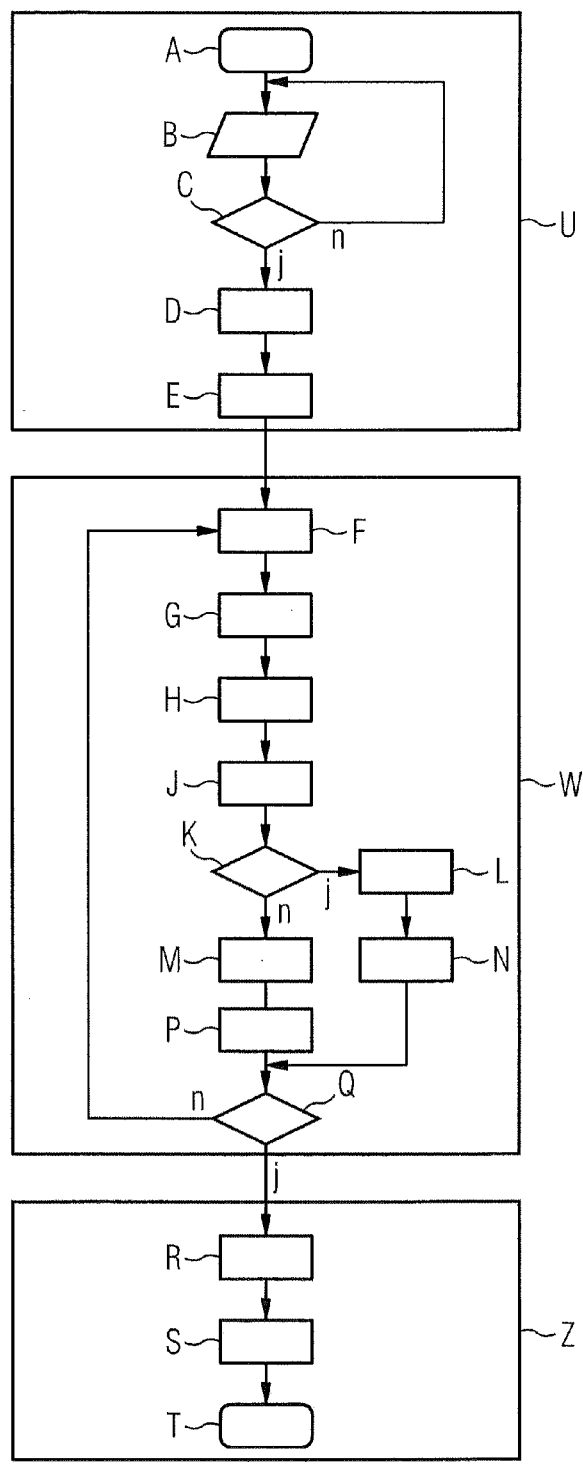
FIG. 13 shows a schematic flowchart of an example embodiment of a method according to the invention for determining a center line.

For a more detailed explanation, FIG. 13 shows a schematic flowchart which again visualizes the essential method steps for identifying the center line:

The method is subdivided into an initializing phase U, a generating phase W for generating a vessel model and a post-processing phase Z.

The method starts at A in the initializing phase U. First of all, a start point 5 (cf. FIG. 1) is entered at an input B—either manually via a user interface or automatically with the aid of input logic. A query C establishes whether the start point 5 is suitable for carrying out the method, that is to say primarily whether it is located within the hollow organ section, but also whether the start point 5 is situated in or in the vicinity of a branching region. If neither condition is the case (n), a return is made to step B; otherwise (j) the method can proceed. In addition, optional steps D and E are possible. In step D an "artificial" branching recognition is carried out which can for example be implemented as a method for branching recognition as described above. It is an artificial branching recognition because it is either already obvious that no real branching is present due to an earlier clarification, or because otherwise at least three vessel segments could be determined if a real branching was present, with the hollow organ extending in the directions of said segments. That is to say, this artificial branching recognition D is only used to determine, in step E, the vessel segments in both main directions of extent of the hollow organ 1, along which directions the center line profile can subsequently be determined further using an A* method.

The generating phase W is started by a selection step F which involves selecting that vessel segment along the direction of which the center line is intended to be determined from the start point 5. The center line is preferably determined from two sides, i.e. toward one another from two start points 5 such that the two most suitable vessel segments are selected from a total of four. Search beams from the start point 5 are defined in step G and the local thresholds for the region around the start point 5 are determined in step H on the basis of the intensity values of the voxels of all search beams. This is then followed in step J by a branching recognition according to the invention with the aid of the method described in more detail above using the region growing method. A query K clarifies whether such a branching is present. If a branching is present (j), it is identified in more detail in a step L, as are the branching hollow organ strands in step N. In particular, this includes determining branching center points 11 and initial center points 15.

By contrast, if there is no branching (n), the next point on the center line is determined in a step M. This is preferably effected with the aid of fitting an ellipsoid into the hollow organ (step P). A query Q determines whether the examination has already reached the end of the hollow organ section. If not (n), the method is recursively repeated from step F, but if it has (j), there is a transition to the post-processing Z in which the center line is extracted in step R with the aid of the individual center points of the geometric figures (cf. FIG. 5) fitted into the hollow organ section and the branching center points 11, and possibly the initial center points 15 of the hollow organ strands; and said center line is optionally post-processed in step S, for example by harmonic shaping of a curved curve to the straight connections between the individual center points. With this, the method is completed at T.

FIG. 14 shows a schematic block diagram of an image processing device 17 with an example embodiment of a branching determination device 23 according to the invention which is arranged within a center line determination device 22 together with center line identification units 24. In addition to the center line determination device 22, the image processing device 17 has an image processing unit 21 and an image output device 19.

Initial image data ABD is supplied to the image processing device 17 and processed in the image processing unit 21. Image data BD resulting therefrom which, moreover, can also comprise initial image data ABD is supplied to both the image output device 19, for example a monitor of a diagnostic station, and the center line determination device 22 as well as, indirectly, the branching determination device 23.

In addition to an input interface 25 and an output interface 37, the branching determination device 23 has the following components: a setting unit 27, a threshold determination unit 29, a region growing unit 31, a connectivity analysis unit 33 and a localization unit 35.

A center line of the hollow organ is identified from the image data BD in the center line identification units 24 of the center line determination device 22, e.g. those units which are designed such that they can carry out a method for identifying the center line as described above. In order to verify that there is no branching at identified points in the hollow organ, said device transfers the corresponding image data to the branching determination device 23, into which said data is supplied via the input interface 25.

The setting unit 27 sets start points 5 within a hollow organ 1. It can be designed merely as an input interface, by means of which user inputs and/or inputs from other logic units, possibly combined with database information, can be supplied, but it can also be designed as an independent or semi-automatic logic unit. Starting from the start points set by the setting unit 27, the threshold determination unit 29 determines the local thresholds $S_u$, $S_o$ in the region around a start point 5, for example on the basis of an analysis of the pixels or voxels in a neighborhood region around the start point 5. The region growing unit 31 carries out a region growing method with the aid of these thresholds $S_u$, $S_o$. The connectivity analysis unit 33 analyzes the connectivity of a number of outer growth layers and the localization unit 35 localizes a branching V as a function thereof. The information relating to the branching is then passed back, via the output interface 37, to the center line identification units 24, which use the information for the further identification of the center line of the hollow organ.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

Finally, reference is again made to the fact that the method described in detail above and the illustrated apparatus are merely example embodiments which can be modified in a wide variety of ways by a person skilled in the art without departing from the scope of the invention. Furthermore, the use of the indefinite article "a" or "an" does not preclude the relevant features from also being present in plural form.

What is claimed:

1. A method for localizing a branching within a hollow organ in image data representing a spatial structure of the hollow organ, the method comprising:
    setting a start point within the hollow organ;
    determining, by an image processing device, at least one local threshold which corresponds to a presence of a wall of the hollow organ;
    carrying out a region growing method to generate growth layers using the determined at least one local threshold, each growth layer being comprised of pixels or voxels representing the hollow organ;
    analyzing connectivity of pixels or voxels in at least one growth layer from among the growth layers to determine whether the pixels or voxels of the at least one growth layer have touching edge portions throughout the growth layer;
    identifying the branching if the connectivity analysis indicates that at least two adjacent ones of the pixels or voxels of the at least one growth layer do not have touching edge portions;
    determining a branching center point from spatial information of the identified branching; and
    generating an image based on the identified branching and the determined branching center point.

2. The method as claimed in claim 1, wherein a plurality of radial search beams are defined from the start point for determining the at least one local threshold and intensity values of at least one of pixels and voxels are determined along the plurality of radial search beams.

3. The method as claimed in claim 2, wherein a histogram is analyzed for determining the at least one local threshold.

4. The method as claimed in claim 3, wherein the histogram analysis comprises estimating the at least one local threshold using a maximum likelihood method.

5. The method as claimed in claim 1, wherein a histogram is analyzed for determining the at least one local threshold.

6. The method as claimed in claim 5, wherein the histogram analysis comprises estimating the at least one local threshold using a maximum likelihood method.

7. The method as claimed in claim 1, wherein the at least one growth layer is a number of outer growth layers from among the plurality of growth layers.

8. The method as claimed in claim 1, wherein the connectivity is analyzed beyond a defined at least one of pixel and voxel spacing between the at least one growth layer and the start point.

9. The method as claimed in claim 1, wherein the connectivity analysis comprises cluster analysis with a distance function.

10. The method as claimed in claim 1, wherein the branching center point is defined by a centroid of all growth layers from the plurality of growth layers constructed up to the detection of the branching.

11. The method as claimed in claim 10, further comprising:
    determining an initial center point of a hollow organ strand, after the branching, from the spatial information of the identified branching.

12. The method as claimed in claim 11, wherein the initial center point of the hollow organ strand is formed as a function of the centroid of a cluster of a number of outer growth layers from among the plurality of growth layers, and wherein the cluster is formed by those local parts of growth layers which are situated in the region of an individual hollow organ strand and no longer form a connected growth layer within the scope of the region growing method.

13. The method as claimed in claim 11, further comprising:
    determining a center line of a section of a hollow organ in image data in a region of the identified branching point of the hollow organ, wherein the center line is directed at least one of through the determined branching center point and through the initial center point.

14. The method as claimed in claim 12, further comprising:
    determining a center line of a section of a hollow organ in image data in a region of the identified branching of the hollow organ, wherein the center line is directed at least one of through the determined branching center point and through the initial center point.

15. The method as claimed in claim 14, wherein a computer program product, which can be loaded directly into a processor of a programmable image processing device, the computer program product including a non-transitory computer readable medium containing computer instructions stored therein for causing the processor to perform the method.

16. The method as claimed in claim 1, wherein a computer program product, which can be loaded directly into a processor of a programmable image processing device, the computer program product including a non-transitory computer readable medium containing computer instructions stored therein for causing the processor to perform the method.

17. The method as claimed in claim 1, further comprising:
determining an initial center point of a hollow organ strand, after the branching, from the spatial information of the identified branching.

18. The method as claimed in claim 17, wherein the initial center point of the hollow organ strand is formed as a function of the centroid of a cluster of a number of outer growth layers from among the plurality of growth layers, and wherein the cluster is formed by those local parts of growth layers which are situated in the region of an individual hollow organ strand and no longer form a connected growth layer within the scope of the region growing method.

19. The method as claimed in claim 1, wherein a non-transitory computer readable medium including program segments for, when executed on a computer device, causing the computer device to implement the method.

20. A branching determination device for determining a branching point within a hollow organ, comprising:
- an input interface for image data representing a spatial structure of the hollow organ;
- a start point setting unit for setting a start point within the hollow organ;
- a threshold determination unit for determining at least one local threshold in a region around the start point;
- a region growing unit for carrying out a region growing method to generate growth layers using the determined at least one local threshold, each growth layer being comprised of pixels or voxels representing the hollow organ;
- a connectivity analysis unit for analyzing connectivity of pixels or voxels in at least one growth layer from among the growth layers to determine whether the pixels or voxels of the at least one growth layer have touching edge portions throughout the at least one growth layer;
- a localization unit for identifying the branching point if the connectivity analysis indicates that at least two adjacent ones of the pixels or voxels of the at least one growth layer do not have touching edge portions;
- a determiner for determining a branching center point from spatial information of the identified branching; and
- an image generator for generating an image based on the identified branching and the determined branching center point.

21. An image processing device comprising:
an image output device; and
a branching determination device for determining a branching point within a hollow organ, including:
- an input interface for image data representing a spatial structure of the hollow organ;
- a start point setting unit for setting a start point within the hollow organ;
- a threshold determination unit for determining at least one local threshold in a region around the start point;
- a region growing unit for carrying out a region growing method to generate growth layers using the determined at least one local threshold, each growth layer being comprised of pixels or voxels representing the hollow organ;
- a connectivity analysis unit for analyzing connectivity of pixels or voxels in at least one growth layer from among the growth layers to determine whether the pixels or voxels of the at least one growth layer have touching edge portions throughout the at least one growth layer;
- a localization unit for identifying the branching point if the connectivity analysis indicates that at least two adjacent ones of the pixels or voxels of the at least one growth layer do not have touching edge portions;
- a determiner for determining a branching center point from spatial information of the identified branching; and
- an image generator for generating an image based on the identified branching and the determined branching center point.

* * * * *